United States Patent [19]

Cowherd, III et al.

[11] 4,187,383
[45] Feb. 5, 1980

[54] PROCESS FOR PRODUCING LOW COLOR RESIDUE ACRYLATE ESTERS

[75] Inventors: Frank G. Cowherd, III; Louis F. Theiling, Jr., both of Charleston, W. Va.

[73] Assignee: Union Carbide Corporation, New York, N.Y.

[21] Appl. No.: 755,046

[22] Filed: Dec. 28, 1976

[51] Int. Cl.$^2$ .................. C07C 69/54; C07C 69/66
[52] U.S. Cl. .................................. 560/224; 560/185
[58] Field of Search ........................... 560/224, 185

[56] References Cited

U.S. PATENT DOCUMENTS

| | | | |
|---|---|---|---|
| 3,178,380 | 4/1965 | Porret | 560/224 |
| 3,594,410 | 7/1971 | Cohen et al. | 560/224 |
| 3,647,737 | 3/1972 | Dowbenko et al. | 560/224 |

*Primary Examiner*—Paul J. Killos
*Attorney, Agent, or Firm*—Stanley Ktorides

[57] ABSTRACT

Low color residue acrylate esters are produced by reacting an organic polyol such as neopentyl glycol, pentaerythritol, or 3'-hydroxy-2',2'-dimethylpropyl 3-hydroxy-2,2-dimethylpropionate with acrylic or methacrylic acid in contact with a lower alkoxy substituted phenolic or alkylated alkoxyphenolic polymerization inhibitor at a critical low reaction temperature of from 20° C. to 80° C.

8 Claims, No Drawings

PROCESS FOR PRODUCING LOW COLOR RESIDUE ACRYLATE ESTERS

BACKGROUND OF THE INVENTION

There are disclosed in the prior art many acrylate esters of organic polyols which are useful as polymerizable monomers. Certain acrylate esters of organic polyols, such as neopentyl glycol diacrylate and the diacrylate compounds described in U.S. Pat. No. 3,645,984 (e.g., 3'-acryloxy-2',2'-dimethylpropyl 3-acryloxy-2,2-dimethylpropionate), are particularly useful in forming hard, mar-resistant coatings. However, problems have been encountered in preparing acrylate esters such as these in that the acrylyl moieties tend to undergo polymerization under the same conditions which promote the esterification reaction between the polyol and acrylic or methacrylic acid.

The prior art discloses preferred reaction temperatures for esterification reactions between acrylic or methacrylic acid and "higher" alcohols (i.e., more than 3 carbon atoms) of greater than 95° C. (see, e.g., U.S. Pat. No. 3,645,984 and Canadian Pat. No. 768,651). The polymerization inhibitors which are effective at inhibiting polymerization of the acrylyl moiety at temperatures above 95° C. (e.g., phenothiazine, methylene blue, and hydroquinone) impart color to the reaction product, which color is difficult to remove by means other than distilling the product. However, many of the acrylate esters of higher alcohols can only be conveniently recovered as residue products, thus, it is difficult to produce residue acrylate esters of organic polyols having low color (i.e., less than 4.0 Gardner) by processes of the prior art. This has largely excluded the use of residue acrylate esters which have otherwise excellent coating properties from uses where it is desired to produce a clear, colorless coating.

SUMMARY OF THE INVENTION

The present invention provides a convenient process for producing low color residue acrylate esters of certain organic polyols. In accordance with the process of our invention, an organic polyol is esterified by reacting it with acrylic or methacrylic acid at a critical low temperature of from 20° C. to 80° C., and preferably from 55° C. to 75° C. We have found that the esterification reaction can be efficiently carried out at these low temperatures in the presence of low-coloring polymerization inhibitors which are not consistently effective at the higher temperatures disclosed in the prior art for esterification of higher alcohols.

DETAILED DESCRIPTION OF THE INVENTION

The organic polyols which are useful in the process of this invention have the structure

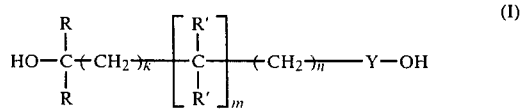

wherein each R individually is hydrogen, alkyl of 1 to 8 carbon atoms such as methyl, ethyl, isobutyl and the like, cycloalkyl having from 5 to 8 carbon atoms such as cyclopentyl, cyclohexyl, cycloheptyl, and cyclooctyl, or aryl of up to 8 carbon atoms such as phenyl, benzyl, and the like; each R' individually is any one of the substituents which R can be or $-CH_2OH$; k, m, and n are integers having a value of from 0 to 5; and Y is nothing or

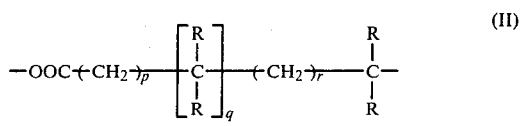

wherein p, q, and r are integers from 0 to 5 and each R is as defined above; provided that when Y is nothing, m and n have values of at least 1 and each R' is a substituent other than hydrogen, and provided further that when R' is $-CH_2OH$, Y is nothing and m is one.

Illustratively, when Y is nothing the organic polyol can be neopentyl glycol or pentaerythritol and when Y is the moiety illustrated in formula II the organic polyol can be 3'-hydroxy-2',2'-dimethylpropyl 3-hydroxy-2,2-dimethylpropionate.

In accordance with the process of this invention, the organic polyol described above is reacted with acrylic or methacrylic acid at a critical low temperature of from 20° C. to 80° C., preferably from 55° C. to 75° C. in contact with a lower alkoxy substituted phenolic or lower alkylated alkoxyphenolic polymerization inhibitor to produce a residue acrylate ester of low color.

The acrylic or methacrylic acid and the organic polyol are reacted in a respective equivalent ratio of from 2:1 to about 3:1.

The esterification reaction is carried out in contact with one of the acid catalysts which are known to those skilled in the art to be useful esterification catalysts. One can mention as illustrative thereof sulfuric acid, toluenesulfonic acid, alkylsulfonic acids and hydrochloric acid. This list is meant to be illustrative only and not to exclude any other suitable acid catalysts known to those skilled in the art. The skilled worker will know the concentrations at which such catalysts are effective. Typically, they are employed at concentrations from about 1% to 20%, based on the moles of the polyol.

The low-coloring polymerization inhibitors employed in our process are lower alkoxy substituted phenolic or lower alkylated alkoxyphenolic inhibitors having up to 10 carbon atoms in the alkyl and alkoxy groups, which can be straight or branched chain. Those skilled in the art will recognize which polymerization inhibitors are within this definition without further description. However, one can mention as exemplary of such inhibitors the monoalkyl ethers of hydroquinone such as monomethyl ether of hydroquinone, monoethyl ether of hydroquinone, mono-t-butyl ether of hydroquinone, and the like; the alkylated hydroxyanisoles such as butylated hydroxyanisole, propylated hydroxyanisole, and the like; or mixtures of these. The preferred polymerization inhibitors are the monoalkyl ethers of hydroquinone, the most preferred being monomethyl ether of hydroquinone. The polymerization inhibitor is used at a concentration of from about 50 ppm to about 5,000 ppm, preferably from 100 ppm to 800 ppm, based on the weight of the acrylic or methacrylic acid.

Since the efficiency of the aforementioned polymerization inhibitors is enhanced by the presence of oxygen, it is desirable to have oxygen present in the esterification reaction mixture. This can be conveniently achieved by sparging air or oxygen through the reaction mixture. We prefer to sparge air through the reaction mixture at a rate of from 10 to 20 percent of the reaction mixture volume per hour.

There can be present in the esterification reaction mixture up to about 50 weight percent of a solvent which will form an azeotrope with the water of esterification, thus facilitating its separation from the acrylate ester reaction product. Such solvents are well known and include, for example, hexane, toluene, xylene, pentane, cyclopentane, cyclohexane, benzene, or mixtures of these. In a preferred embodiment of the invention, the reaction is carried out at a temperature and pressure such that the azeotrope formed by the solvent and water of esterification is continually being vaporized and thereby removed from the reaction mixture, providing that the temperature of reaction is within the aforementioned limits of this invention. The vapor of the azeotrope can then be condensed, the water separated by any convenient means such as a Dean-Stark water separator, and the solvent recycled to the reaction mixture.

Pressure of reaction is not critical and the reaction proceeds satisfactorily at atmospheric pressure. When one employs the above described method of azeotropically removing water of esterification during the reaction, it may be necessary to conduct the reaction at somewhat reduced pressure to vaporize the azeotrope and yet maintain the critical low reaction temperature range of this process. Of course, this will depend on the particular solvent chosen and those skilled in the art will know the suitable temperatures and pressures at which the water azeotropes of various solvents can be vaporized.

The reaction is continued until all the hydroxyl groups of the organic polyol have been esterified or until all the acrylic or methacrylic acid has been reacted. The acrylate ester can be conveniently recovered by known means such as neutralization of excess acid, physical separation of the organic phase containing the residue acrylate ester, and stripping of solvent from the organic phase.

The residue acrylates produced by the process of this invention are useful in the formation of polymers, either alone or copolymerized with other ethylenically unsaturated monomers. The resultant polymers have a broad variety of uses and are especially useful in the formation of hard, mar-resistant coatings. Because of the low color obtainable in the residue acrylate esters produced by the process of this invention, they are particularly useful in clear, colorless coatings.

The following examples are presented by way of further illustration of the invention described herein and are not intended to limit the invention in any way. Unless otherwise stated, all parts and percents are by weight. The designation MMHQ is used in lieu of the more complete nomenclature monomethyl ether of hydroquinone and BHA is used in lieu of butylated hydroxyanisole.

EXAMPLE 1

Preparation of neopentyl glycol diacrylate

A series of preparations of neopentyl glycol diacrylate were carried out, each employing the following procedure. To a three-neck 1,000 ml. flask fitted with a mechanical stirrer, air sparge tube, and a 5-tray Oldershaw distillation column having a water-cooled condenser and a Dean-Stark water separator at its overhead were charged 104 parts of neopentyl glycol and an amount of solvent as indicated in the table below. There were then added, while heating to reflux, 158 parts of glacial acrylic acid which contained 200 ppm, based on acrylic acid weight, of MMHQ as a polymerization inhibitor (except where no MMHQ is indicated in the table), para-toluenesulfonic acid in an amount indicated in the table, and an additional amount of MMHQ or BHA as indicated in the table. An air sparge was started at a rate of 23% of the reaction mixture volume per hour before the reactants reached 30° C. The reactants were heated to the temperature indicated in the table under a sufficiently reduced pressure to allow reflux of the azeotrope of hexane and water of esterification. The mixture was refluxed until 34–36 parts of water of esterification had been removed. The reaction mixture was then neutralized to pH 7.0–7.5 by the addition of a 15% solution of NaOH in water. The phases were allowed to separate and the aqueous phase was drawn off and discarded. The residue acrylate ester was then isolated by stripping solvent from the organic phase, first at a maximum temperature of 45° C. and lowest obtainable vacuum to remove most of the solvent, and finally at 50° C. and less than 10 mm. Hg pressure to remove traces of solvent. The remaining product was cooled and filtered to obtain neopentyl glycol diacrylate. The reaction conditions and analytical characterizations of the products are given in the table below.

In all of the preparations of neopentyl glycol diacrylate, gas chromatographic analysis of the product indicated the presence of minor amounts of byproducts identified as neopentyl glycol monoacrylate, 3'-acryloxy-2',2'-dimethylpropyl 3-acryloxypropionate, and 3'-acryloxy-2',2'-dimethylpropyl 3-(3''-acryloxy-2'',2'''-dimethylpropyloxy)propionate. While these byproducts can be separated by known methods, separation is not normally performed, since it is slow and the byproducts do not adversely affect the end use properties of the neopentyl glycol diacrylate.

| Reaction temp., °C. | pTSA, mole % | MMHQ[1], ppm | BHA[1], ppm | Solvent type[2] | wt. %[3] | Reaction time, hrs. | Yield, %[4] | Color Gardner | Viscosity, cps. | Specific gravity |
|---|---|---|---|---|---|---|---|---|---|---|
| 45 | 3 | 800 | — | Tol. | 36 | 35 | 73 | <1 | 8.1 | 1.030 |
| 48 | 3 | 800 | — | Tol. | 36 | 30 | 73 | <1 | 7.1 | 1.031 |
| 53 | 6 | 800 | — | Tol. | 36 | 11 | 85 | 1 | — | 1.016 |
| 51 | 12 | 800 | — | Tol. | 36 | 5 | 83 | <2 | 7 | 1.026 |
| 53–55 | 12 | 800 | — | Tol. | 36 | 12 | 87.5 | 1 | 7 | 1.027 |
| 50–60 | 12 | 800 | — | Tol. | 36 | 12 | 89 | 2 | 5.9 | 1.026 |
| 68–77 | 6 | 800 | — | Hex. | 30 | 8 | 96 | <1 | 8 | — |
| 65–74 | 6 | 800 | — | Bz. | 30 | 8 | 97.5 | 3 | 9 | 1.025 |
| 66–74 | 6 | 800 | — | Hex | 30 | 8.5 | 97.5 | 2 | 8 | 1.027 |
| 60–78 | 6 | 800 | — | Bz. | 30 | 9 | 97.4 | 3.5 | 8.25 | 1.027 |
| 77–79 | 1 | 800 | — | Iso. | 50 | 9 | 93.5 | 3.5 | 9 | 1.026 |
| 50 | 6 | 800 | — | Hex. | 30 | 19.5 | 93.4 | <1 | 9 | 1.026 |
| 73 | 6 | 200 | — | Hex. | 30 | 6.0 | 95.7 | <1 | 8 | 1.024 |

-continued

| Reaction temp., °C. | pTSA, mole % | MMHQ[1], ppm | BHA[1], ppm | Solvent type[2] | wt. %[3] | Reaction time, hrs. | Yield, %[4] | Color Gardner | Viscosity, cps. | Specific gravity |
|---|---|---|---|---|---|---|---|---|---|---|
| 73 | 6 | — | 200 | Hex. | 30 | 9.0 | 87.2 | <1 | 7.25 | 1.025 |
| 73 | 6 | — | 200 | Hex. | 30 | 9.5 | 96.2 | <1 | 8 | 1.025 |
| 68–72 | 6 | — | 200 | Hex. | 30 | 7.5 | 79.3 | <1 | 8 | 1.026 |
| 68–72 | 6 | 300 | — | Hex. | 30 | 9.0 | 90 | <1 | 9 | 1.026 |

[1] Based on acrylic acid weight
[2] Tol. = toluene
Bz. = benzene
Hex. = hexane
Iso. = isopropyl ether
[3] Based on total reaction mixture
[4] Residue product as weight percent of stoichiometrically calculated neopentyl glycol diacrylate yield.

EXAMPLE 2

Preparation of 3'-acryloxy-2',2'-dimethylpropyl 3-acryloxy-2,2-dimethylpropionate To a three neck kettle equipped with a mechanical stirrer, air sparge tube, thermometer, and a 5-tray Oldershaw distillation column having a water-cooled condenser and a Dean-Stark water separator there were charged 204 grams of 3'-hydroxy-2',2'-dimethylpropyl 3-hydroxy-2,2-dimethylpropionate which had previously been purified by distillative removal of impurities, 0.03 grams of MMHQ, 150 grams of hexane, 20.64 grams of para-toluenesulfonic acid, and 158.4 grams of glacial acrylic acid which contained 200 ppm, based on the acrylic acid weight, of MMHQ as a polymerization inhibitor. The mixture was refluxed at 67° C. to 73° C. and atmospheric pressure, with efficient mixing, for 12.5 hours. Air was sparged through the reaction mixture at a rate of 15% of the reaction mixture volume per hour. There were collected in the Dean-Stark water separator 34.75 grams of water of esterification. The reaction mixture was cooled to 25° C. and maintained at that temperature while adding 105 ml. of 15% NaOH in water solution to neutralize excess acid. The organic layer was separated and stripped of solven and water at 50° C. under reduced pressure. The residue product in the kettle weighed 299.5 grams. It was filtered through diatomaceous earth to give a product having a Gardner color of 3, a specific gravity of 1.047, a Brookfield viscosity of 22 cps., an ester number of 2.945, an acrylate number of 1.91, and an acidity of 0.01%. Gas chromatographic analysis indicated that the product contained 72% 3'-acryloxy-2',2'-dimethylpropyl 3-acryloxy-2,2-dimethylpropionate, 13.9% neopentyl glycol diacrylate, 1.6% monoacrylate ester of 3'-hydroxy-2',2'-dimethylpropyl 3-hydroxy-2,2-dimethylpropionate, and 12.5% unknown byproducts.

EXAMPLE 3

Preparation of acrylates of pentaerythritol

A series of preparations were run using a 2-liter, 3-neck flask fitted with a 5-tray Oldershaw distillation column, mechanical stirrer, and an air sparge. In each case, there were charged MMHQ, para-toluenesulfonic acid, pentaerythritol and acrylic acid in the amounts indicated in Table I. An air sparge was started at 15–20% of the reaction mixture volume per hour. The pressure was reduced and the temperature increased to allow toluene to reflux while maintaining a kettle temperature of 70°–72° C. Water of esterification was azeotropically removed during the reaction and collected in the Dean-Stark water separator. Reaction times are indicated in Table I. When the reaction was complete, the reaction mixture was cooled and 20 grams of sodium chloride were added. The reaction mixture was then neutralized with an aqueous NaOH solution. The aqueous layer was removed and the organic layer was concentrated by stripping solvent under reduced pressure at a maximum temperature of 50° C. Analytical characterization of the remaining residue products are given in Table II.

TABLE I

Esterification of Pentaerythritol[1]

| Run | MMHQ,[2] ppm | Toluene,[3] % | AA/PE[4] | Reaction Time, hrs. | Reaction Temp. °C. | Water,[5] grams | NaOH Sol'n. %[6] | NaOH Sol'n. ml. | NaCl[7] Sol'n. | Residue product, grams |
|---|---|---|---|---|---|---|---|---|---|---|
| 1 | 600 | 40 | 3.7 | 5 | 71 | 60 | 5 | 302 | No | 264 |
| 2 | 600 | 40 | 3.7 | 4 | 71 | 53 | 5 | 940 | Yes | 231 |
| 3 | 800 | 50 | 3.7 | 6 | 72 | 50 | 5 | 878 | No | 205 |
| 4 | 800 | 30 | 3.5 | 7 | 72 | 53 | 5 | 280 | Yes | 189 |
| 5 | 800 | 30 | 4.16 | 3.5 | 71 | 59 | 5 | 1050 | Yes | 252 |
| 6 | 800 | 50 | 4.16 | 6 | 70 | 57 | 15 | 258 | Yes | 292 |
| 7 | 800 | 30 | 3.5 | 4.3 | 70 | 48 | 20 | 226 | Yes | 189 |
| 8 | 800 | 30 | 4.16 | 3 | 70 | 49 | 20 | 340 | Yes | 198 |
| 9 | 800 | 30 | 3.5 | 4.2 | 72 | 56 | 15 | 156 | Yes | 268 |
| 10 | 800 | 18 | 4.4 | 4.3 | 71 | 60 | 20 | 236 | Yes | 267 |
| 11 | 800 | 40 | 3.88 | 8.5 | 70 | 63 | 20 | 120 | Yes | 250 |
| 12 | 800 | 10 | 3.5 | 4.2 | 76 | 59 | 20 | 106 | Yes | 234 |
| 13 | 800 | 30 | 3.83 | 5.2 | 70 | 58 | 20 | 190 | Yes | 244 |
| 14 | 800 | 35 | 4.0 | 5 | 70 | 58 | 20 | 198 | Yes | 259 |

TABLE I-continued

| | | | Esterification of Pentaerythritol[1] | | | | | | |
|---|---|---|---|---|---|---|---|---|---|
| Run | MMHQ,[2] ppm | Toluene,[3] % | AA/PE[4] | Reaction Time, hrs. | Reaction Temp. °C. | Water,[5] grams | NaOH Sol'n. %[6] | NaOH Sol'n. ml. | NaCl[7] Sol'n. | Residue product, grams |
| 15 | 800 | 48 | 4.16 | 6 | 72 | 60 | 20 | 190 | Yes | 280 |

[1]One mole of pentaerythritol using 18 mole % p-toluenesulfonic acid as catalyst.
[2]Based on acrylic acid wt.
[3]Based on total reaction mixture wt.
[4]Mole ratio of acrylic acid to pentaerythritol.
[5]Water of esterification.
[6]Wt. % NaOH in water solution employed.
[7]Saturated aqueous NaCl sol'n. used to reduce extraction of product into aqueous phase.

TABLE II

| | Residue Acrylate of Pentaerythritol - Analysis | | | | | |
|---|---|---|---|---|---|---|
| Run | Gardner Color | Viscosity,[1] cks. | Functionality, av. Ester | Acrylate | % Tetraacrylate[2] | % Triacrylate[2] |
| 1 | — | 362 | — | — | — | — |
| 2 | — | 120 | — | — | — | — |
| 3 | 2 | 458 | 3.01 | 2.61 | 66 | 34 |
| 4 | — | — | — | — | — | — |
| 5 | 1 | 112 | 2.99 | 2.83 | 45 | 55 |
| 6 | 1 | 278 | 3.01 | 2.82 | 64 | 36 |
| 7 | 1 | 161 | 3.05 | 2.93 | 49 | 51 |
| 8 | 1 | 149 | 3.06 | 2.94 | 39 | 61 |
| 9 | 1 | 289 | 3.07 | 2.83 | 56 | 44 |
| 10 | 1 | 153 | 3.01 | 2.97 | 50 | 50 |
| 11 | 1 | 536 | 3.11 | 2.73 | 74 | 26 |
| 12 | 1 | 243 | 3.08 | 2.84 | 54 | 46 |
| 13 | 1 | 212 | 3.08 | 2.87 | 54 | 46 |
| 14 | 1 | 193 | 3.05 | 2.86 | 48 | 52 |
| 15 | 1 | 190 | 3.13 | 2.91 | 58 | 42 |

[1]@ 100° F.
[2]By gas chromatography in a 10 ft. column of 10% OV 101 on Chromasorb W.

What is claimed is:

1. In an esterification process whereby acrylic or methacrylic acid is reacted with an organic polyol of the formula

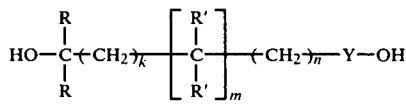

wherein each R is hydrogen, alkyl of 1 to 8 carbon atoms, or cycloalkyl from 5 to 8 carbon atoms; each R' is hydrogen, alkyl of 1 to 8 carbon atoms or —CH$_2$OH; K, m, and n are integers from 0 to 5; and Y is nothing or

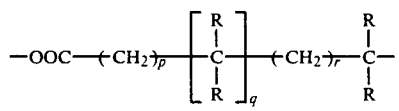

wherein p, q, and r are integers from 0 to 5 and each R is as defined above, provided that when Y is nothing, m and n have values of at least 1 and each R' is a substituent other than hydrogen, and provided further that when R' is —CH$_2$OH, Y is nothing and m is 1, and wherein the acrylate or methacrylate ester product is recovered as a non-distillable residue, the improvement which comprises carrying out the esterification reaction at a temperature of from 20° C. to 80° C. with the reactants in contact with from 50 p.p.m. to 5,000 p.p.m., based on the weight of acrylic or methacrylic acid, of an alkoxy substituted phenolic or alkylated alkoxyphenolic polymerization inhibitor having up to 10 carbon atoms in the alkyl and alkoxy segments, to produce a product having a Gardner color of 4 or less.

2. A process as claimed in claim 1, wherein said organic polyol is neopentyl glycol.

3. A process as claimed in claim 1, wherein said organic polyol is 3'-hydroxy-2',2'-dimethylpropyl 3-hydroxy-2,2-dimethylpropionate.

4. A process as claimed in claim 1, wherein said esterification reaction is carried out at a temperature of from 55° C. to 75° C.

5. A process as claimed in claim 1, wherein said alkoxy substituted phenolic or alkylated alkoxyphenolic polymerization inhibitor is chosen from the group consisting of monoalkyl ether of hydroquinone having up to 10 carbon atoms in the alkyl segment and alkylated hydroxyanisole having up to 10 carbon atoms in the alkyl segment.

6. A process as claimed in claim 1, wherein said alkoxy substituted phenolic or alkylated alkoxyphenolic polymerization inhibitor is monomethyl ether of hydroquinone.

7. A process as claimed in claim 1, wherein air is sparged through the esterification reaction mixture at a rate of from 10% to 20% of the reaction mixture volume per hour.

8. A process as claimed in claim 1, wherein said alkoxy substituted phenolic or alkylated alkoxyphenolic polymerization inhibitor is employed at a concentration of from 100 ppm to 800 ppm, based on the weight of the acrylic or methacrylic acid.

* * * * *